United States Patent [19]

Yelvington

[11] Patent Number: 5,336,862
[45] Date of Patent: Aug. 9, 1994

[54] APPARATUS FOR DESTROYING SYRINGE-TYPE NEEDLES BY ELECTRICAL CURRENT

[75] Inventor: Richard D. Yelvington, Jacksonville, Fla.

[73] Assignee: Inventive Services, Inc., Jacksonville, Fla.

[21] Appl. No.: 75,670

[22] Filed: Jun. 11, 1993

Related U.S. Application Data

[63] Continuation-in-part of Ser. No. 981,775, Nov. 25, 1992.

[51] Int. Cl.$^5$ ............................................. B23K 11/22
[52] U.S. Cl. ......................................................... 219/68
[58] Field of Search ............................ 219/68; 110/250

[56] References Cited

U.S. PATENT DOCUMENTS

| | | | |
|---|---|---|---|
| 4,628,169 | 12/1986 | Ch'ing-Lung | 219/68 |
| 4,860,958 | 8/1989 | Yerman | 241/23 |
| 4,877,934 | 10/1989 | Spinello | 219/68 |
| 4,961,541 | 10/1990 | Hashimoto | 219/68 |
| 4,965,426 | 10/1990 | Colombo | 219/68 |
| 4,969,379 | 11/1990 | Taylor | 83/167 |
| 5,076,178 | 12/1991 | Kohl et al. | 219/68 |
| 5,091,621 | 2/1992 | Butler | 219/68 |
| 5,138,124 | 8/1992 | Kirk et al. | 219/68 |
| 5,138,125 | 8/1992 | Salesses | 219/68 |
| 5,212,362 | 5/1993 | Burden et al. | 219/68 |
| 5,245,935 | 9/1993 | Fukuda | 219/68 |

Primary Examiner—Geoffrey S. Evans
Attorney, Agent, or Firm—Deveau, Colton & Marquis

[57] ABSTRACT

An apparatus and method for destroying or rendering safe the metal needle portion of a hypodermic needle syringe in which the needle is destroyed by electrical resistance heating, the apparatus having complimentary electrodes which contact only the end one-eighth inch to three-sixteenths inch (⅛"-3/16") portion of the needle until the needle hub contacts the first electrode, at which point the first electrode is slidably movable toward the second electrode allowing the destruction of the remaining portion of the needle, the method being the progressive destruction of the end one-eighth to three-sixteenths (⅛"-3/16") portion of the needle until the hub portion of the needle contacts the first electrode, at which time the first electrode slidably moves toward a second electrode allowing the destruction of the remaining one-eighth to three-sixteenths inch (⅛"-3/16") of the needle.

6 Claims, 3 Drawing Sheets

APPARATUS FOR DESTROYING SYRINGE-TYPE NEEDLES BY ELECTRICAL CURRENT

This is a continuation-in-part of copending application Ser. No. 07/981,775 filed on Nov. 25, 1992.

BACKGROUND OF THE INVENTION

1. Field of the Invention

This invention relates generally to the field of sterilizing and destroying the hypodermic needle component of a syringe so as to render it safe for disposal. This invention relates specifically to a self-contained apparatus which vaporizes and sterilizes the hypodermic needle component of the syringe by passing electricity continuously along portions of the needle component until significantly all of the needle portion has been burned due to the heat produced by the electrical resistance through the needle component, with the resistance heat also sterilizing any remaining portions of the needle component.

2. Prior Art

Current medical practice favors one-time use hypodermic needle syringes over reuseable syringes. After a one-time use hypodermic needle syringe has been used, it must be disposed of properly. A used hypodermic needle syringe often poses a health hazard to any person coming into contact with a contaminated needle or syringe. The widespread exposure of contagious and fatal diseases multiplies this danger.

The most common method for disposing of used hypodermic needle syringes is a "sharps" container. A sharp's container merely is a plastic container into which the used hypodermic needle syringes are placed. When the container is full, a cap is placed on the container and the container is disposed of. Typically, a service picks up the full sharps' containers and disposes of the full containers either through incineration or in landfills. When destroyed in incinerators, the sharps' container provides a sufficient method of disposal of the used hypodermic needle syringes. However, sharps' containers suffer from several disadvantages. First, the used hypodermic needle syringes are not sterilized before being placed in the sharps' container. This can lead to unintentional contact with a contaminated needle. Second, if the sharps' containers are disposed of in a landfill, there always is the possibility that the sharps' container can inadvertently open or be broken, thus exposing the contaminated needles.

An electrical syringe needle destroyer is disclosed in U.S. Pat. No. 4,628,269 to Ch'ing-Lung. The Ch'ing-Lung device comprises a pair of spaced apart electrodes within a self-contained unit. The needle of the syringe is inserted into an opening in the unit until the base of the needle component is positioned between the two electrodes. When electricity is passed between the electrodes, the electricity causes the portion of the needle between the electrodes to melt, thus severing the needle from the syringe body. The needle portion falls into a collection means and can be disposed. The Ch'ing-Lung device does not destroy the needle, but merely severs the needle from the syringe body. Therefore, the Ch'ing-Lung device does not eliminate the dangers of contamination from the end of the needle, nor the safety hazard obvious from having many loose needle heads in the unit.

A plastic syringe destruction device is disclosed in U.S. Pat. No. 4,860,958 to Yerman. The Yerman device employs a cylinder and piston compaction unit which uses heat to thermally smash complete plastic syringes, including the needle component, into a compacted mass. One or more plastic syringes are placed in the cylinder and the cylinder lid is closed. The syringes then are heated to temperatures between 100° C. and 200° C. to bring about melting of the syringes, as well as sterilization. The piston travels upwardly in the cylinder while the syringes are at temperature, thus compacting the softened or molten plastic syringes into the compacted mass. The Yerman device suffers from several disadvantages, the most important of which is that the syringes are not raised to a temperature high enough to destroy the metal needle portion of the syringe. After the plastic syringes have been compacted into a mass, the metal needles typically protrude from the plastic mass, thus still posing a danger to the operator. Although the needles may have been sterilized, puncture wounds caused by the needles are neither desired nor healthy.

A hypodermic syringe needle destroying and sterilizing apparatus and method is disclosed in U.S. Pat. No. 4,877,934 to Spinello. The Spinello device is aimed specifically at destroying the metal needle portion of the hypodermic syringe by using electrical resistance heating between electrodes. The hypodermic needle is placed in a carrier which contacts the upper portion of the metal needle closest to the syringe barrel. The carrier then carries the syringe over an upwardly sloping second electrode. As the needle point contacts the second electrode, electricity passes from the second electrode through the metal needle into the first electrode, thus causing resistance heating of the metal needle. In theory, the electrical resistance heating melts and destroys the metal needle. However, in practice, the electrical resistance heating generally only softens the metal needle such that as the metal needle contacts the upwardly sloping second electrode, the metal needle bends outward. Although the Spinello device may heat the metal needle to a temperature high enough to sterilize it, typically the metal needle remains and poses the same health and safety hazard any other sharp instrument has. Further, the Spinello device comprises many moving parts which have the potential of jamming and wearing.

A disposable needle and syringe destructor unit is disclosed in U.S. Pat. No. 4,969,379 to Taylor, et al. The Taylor device essentially is a syringe guillotine. The syringe is inserted into a receiving hole a certain distance, and a spring-biased piston is hand actuated forcing a cutting member down on the syringe. The process is repeated until the entire syringe has been cut into smaller portions, which portions fall to the bottom of the container. Obviously, the Taylor device suffers from the disadvantage that the syringe is not sterilized and the metal needle portion, although in smaller pieces, still presents a safety hazard. After the Taylor device is full of syringe portions, it must be disposed of in much the same manner as the sharps' containers.

Therefore, it can be seen that there exists a need for an apparatus for sterilizing and destroying the metal needle component of a hypodermic needle syringe. While past methods destroy a portion of the needle and may sterilize the needle, these devices do not do a complete job of destroying the entire needle component of the syringe, and the used hypodermic needle portion of the syringe is still not safe to the handler or for the environment. The present invention overcomes the disadvantages of the prior art by thoroughly burning and destroying significantly all of the needle portion of the syringe by continuously passing a sufficient amount of electricity through the needle, burning and destroying portions of the needle at a time. Any remaining needle portion, particularly the nub of the needle closest the syringe barrel, also has been heated, through electrical resistance heating, to a sufficient temperature for a sufficient period of time to sterilize any remaining needle portion. Unlike the prior art which acts upon only the base and tip of the needle, the present invention acts only on a small portion of the needle at a time, eliminating the need for the high amperages and voltages required by the prior art, and eliminating the problem of needles breaking between the base and tip and needles welding themselves to the electrodes as frequently occurs in the prior art devices.

BRIEF SUMMARY OF THE INVENTION

The present invention provides an apparatus which destroys significantly all of the metal needle portion of the hypodermic needle syringe, and sterilizes remaining portions of the needle, particularly any nub of the metal needle remaining. The operator inserts the metal needle portion of the hypodermic needle syringe through an opening into the burner unit which comprises two electrodes. The electrodes are generally circular discs of high grade carbon and are spaced apart from each other, preferably one-eighth to three-sixteenths of an inch ($\frac{1}{8}''-3/16''$), in an overlapping relationship relative to the opening, with one of the electrodes located proximal to the opening and one of the electrodes located distal to the opening. Each electrode is rotationally journaled on separate central shafts and are held in their desired starting positions using compression springs. As the needle is inserted through the opening, first the shaft of the needle contacts the circumferential edge of the first proximal electrode, then, as the needle is inserted further through the opening, second, the tip of the needle contacts an upper surface portion of the second distal electrode.

One of the electrodes is connected to the positive terminal of a direct electric current source and the other electrode is connected to the negative terminal of a direct electric current source, in the preferred embodiment. An electrical arc is created across the two electrodes. Since the two electrodes are spaced approximately one-eighth to three-sixteenths of an inch ($\frac{1}{8}''-3/16''$) apart in the preferred embodiment, the electrical arc only acts on this portion of the needle at a time, burning the tip off of the needle continuously as the tip contacts the distal electrode. As the needle is inserted into the opening, one-eighth to three-sixteenths of an inch ($\frac{1}{8}''-3/16''$) of the needle is subjected to the electrical arc at a time, thus eliminating the high amperage and high voltage power sources previously necessary to act on the entire needle length.

Once the needle has been inserted into the opening up to its base where it is attached to the syringe barrel, the base forces the proximal electrode downward on its shaft in the direction of the distal electrode, compressing the first electrode shaft spring, thus lessening the distance between the two electrodes and allowing the remaining portion of the needle to be subjected to the electrical current and burned off at the tip contacting the distal electrode. Once the deneedled syringe is removed from the opening, the first electrode shaft spring returns the first electrode to its starting position. the electrical current has the effect of incinerating the metal needle through resistance heating and/or arcing, thus destroying it. For any portion of the metal needle not incinerated, the electrical arc creates resistance heating of the metal needle to a temperature sufficient to sterilize the metal needle portion, namely greater than 100° C. Any unburned or melted portions of the metal needle are sterilized by the resistance heat and fall into a disposal unit or debris box.

The deneedled hypodermic needle syringe is then removed from the burner unit and can be destroyed using any conventional barrel destruction unit or, preferably, the barrel sterilization and compactor unit disclosed and claimed in the parent application hereto.

Accordingly, it is an object of the present invention to provide an apparatus for destroying metal needles using electrical resistance heating.

Another object of the present invention is to provide an apparatus for destroying the needle component of a syringe by destroying and/or vaporizing the metal needle component of the hypodermic syringe and sterilizing any remaining portion of the needle.

It is another object of the present invention to provide an apparatus for destroying needles which renders any unburned portions of the needle sterile and not harmful to the operator and other humans.

Still another object of the present invention is to provide a syringe needle destroyer which will meet USOSHA requirements and USEPA and hospital approval for a medical device which sterilizes and destroys used hypodermic syringe needles.

Yet another object of the present invention is to provide an apparatus for destroying needles which is a compact, stand alone unit which can be used by hospital wards, individual hospital rooms, doctors' examining rooms, dental or veterinary practices.

It is an object of the present invention to provide an apparatus for destroying needles which is simple and efficient in operation, durable in construction, and ecologically friendly.

Another object of the present invention is to provide an apparatus for destroying needles which uses a lower amperage and lower voltage power source when compared to current art devices, thus using less electricity and being more economical than current art devices.

Still another object of the present invention is to provide an apparatus for destroying needles which renders the entire used syringe safe for handling.

Yet another object of the present invention is to provide an apparatus for destroying needles in which significantly all of the needle is destroyed without the need for a great deal of operator manipulation, thus making the present invention more safe than current art devices.

These objects, and other objects, features and advantages of the present invention, will become more apparent to one skilled in the art when the following detailed description of the preferred embodiment is read in conjunction with the appended figures in which like reference numerals denote like components throughout the several views.

DETAILED DESCRIPTION OF THE PREFERRED EMBODIMENT

Figure 1:
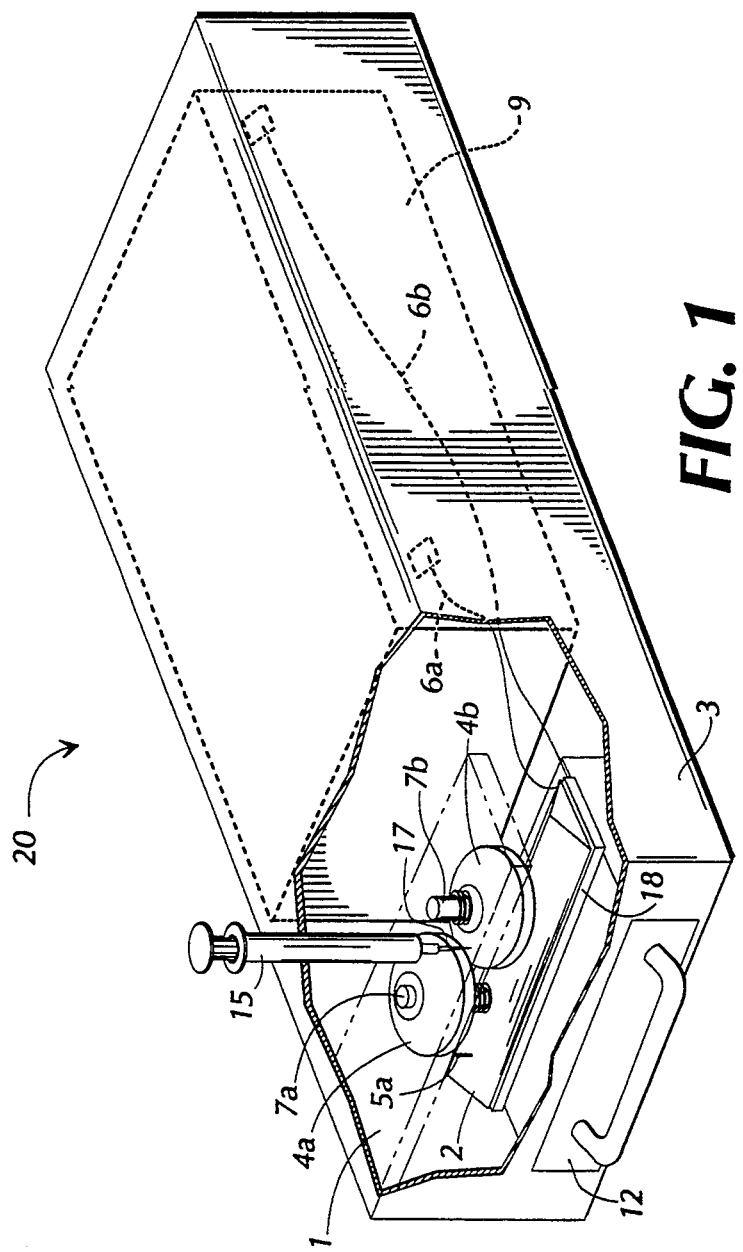
FIG. 1 is a perspective view of the needle destroyer unit.

With reference now to the figures, a preferred embodiment of the needle destruction unit 20 of the present invention will be described by first describing the various components and how they are structurally related to each other and then describing the sequence of operations for destroying a hypodermic syringe needle.

1. Structure of the Invention

The needle destruction unit 20 comprises a relatively small housing 3, generally approximately the size of an electric pencil sharpener assembly, that allows the needle 17 of one syringe 15 at a time to be destroyed. The housing 3 is a generally rectangular cubic hollow structure which contains the needle destroying means, the refuse collection means, and the power means. Housing 3 has a front wall through which a needle debris box 12 may be accessed, a top wall through which an opening 16 is formed providing needle 17 access to the interior of the unit, left, right and back walls relative to the front wall, and a bottom wall.

The needle destroying means comprises two overlapping disc electrodes 4 preferably comprised of high grade carbon. The electrodes 4 may be comprised of any suitable electrode material; however, high grade carbon provides the preferred electrical conduction level and has a satisfactory lifetime. The electrodes 4 are generally disc-like in structure, having an upper surface, a lower surface, a circumferential surface, and a central, axial hole. The upper surface and lower surface of upper or proximal electrode 4a taper toward each other in the direction from the center of the proximal electrode 4a out to the circumferential surface of proximal electrode 4a. The upper surface of lower or distal electrode 4b tapers downward toward the lower surface of distal electrode 4a in the direction from the center of the distal electrode 4b out to the circumferential surface of distal electrode 4b. Each of the electrodes 4 are rotationally and slidably mounted horizontally on vertical standoffs or shafts 7, each electrode 4 being able to slide upwardly or downwardly on its respective shaft 7. Being horizontally mounted on vertical shafts 7, the upper surfaces of the electrodes 4 taper in a downward direction from the centers to the circumferential surfaces of the electrodes 4, the lower surface of proximal electrode 4a tapers in an upward direction from the center to the circumferential surface of proximal electrode 4a, and the lower surface of distal electrode 4b is horizontal.

Shafts 7 are journaled at their upper ends in a first ceramic support structure 1, and at their lower ends in a second ceramic support structure 18. First ceramic support structure 1 is a generally rectangular cubic structure horizontally mounted on the interior surface of the top wall of housing 3. Second ceramic support structure 18 also is a generally rectangular cubic structure mounted at one end to the left wall of housing 3 and at the other end to the right wall of housing 3 such that second ceramic support structure 18 is located directly below first ceramic support structure 1 approximately midway between the top wall and the bottom wall of housing 3.

Located immediately above second ceramic support structure 18 is deflector insulator 2 constructed of an electrically non-conducting material. Deflector insulator 2 has a generally triangular structure much like the roof of a typical house or a ridge. Deflector insulator 2 also is mounted at one end on the left wall of housing 3 and on the other end on right wall of housing 3 and has generally the same horizontal dimensions as second ceramic support structure 18. Deflector insulator has two pass-through holes located along the apex of the structure. As described in more detail below, shafts 7 pass through these two pass-through holes.

Copper pads 11 are mounted on second ceramic support structure 18. Shafts 7 extend downwardly from first ceramic support structure 1 through the pass-through holes in deflector insulator 2, and terminate abutting copper pads 11. Copper pads 11 must not touch each other so that they are electrically insulated from each other on second ceramic support structure 18. Shafts 7 also must be constructed of an electrical conducting material. In this manner, proximal electrode 4a, mounted on shaft 7a which abuts copper pad 11a is electrically insulated from distal electrode 4b which is mounted on shaft 7b, which abuts copper pad 11b.

Helical compression springs 14 are mounted on shafts 7 such that shafts 7 pass through the center of the helix of helical compression springs 14. Spring 14a is mounted on shaft 7a below proximal electrode 4a such that spring 14a is located between proximal electrode 4a and deflector insulator 2. Compression spring 4b is mounted on shaft 7b above distal electrode 4b such that it is located between first ceramic support structure 1 and distal electrode 4b. In this manner, proximal electrode 4a is maintained in a position generally abutting first ceramic support structure 1 by compression spring 4a, and distal electrode 4b is maintained in a position generally abutting deflector insulator 2 by compression spring 4b. Flat washer 13 may be located between distal electrode 4b and deflector insulator 2 as a spacer and to allow freer rotation of distal electrode 4b about shaft 7b. A flat washer 13 also may be located between proximal electrode 4a and first ceramic support structure 1 also to act as a spacer and to allow freer rotation of proximal electrode 4a about shaft 7a.

Figure 4:
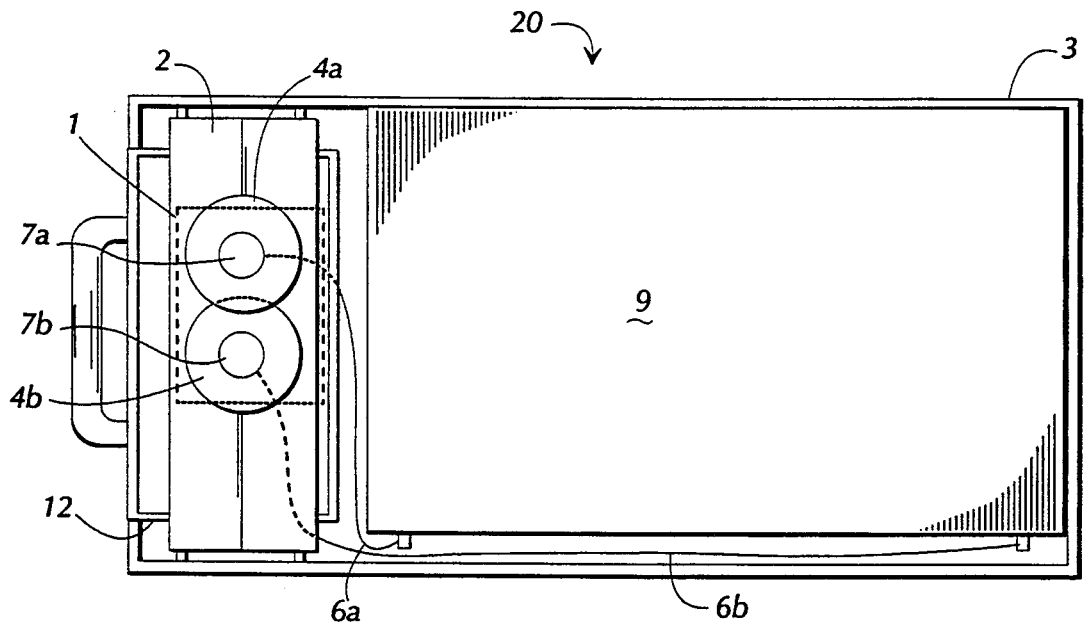
FIG. 4 is a perspective top view, partly in section, of the needle destroyer unit as in FIG. 1 in its starting and operating position showing a hypodermic needle with the metal needle portion inserted into the burner unit.

In the starting and operating position, compression spring 14a forces proximal electrode 4a upwardly against first ceramic support substrate 1 or flat washer 13, if present, and second compression spring 14b forces distal electrode 4b downwardly against deflector insulator 2 or flat washer 13, if present, thus creating a gap of up to one-half inch (½"), and preferably between approximately one-eighth of an inch and three-sixteenths of an inch (⅛"−3/16"), between the lower surface of proximal electrode 4a and the upper surface of distal electrode 4b. As can be seen in greatest detail in FIG. 2a, FIG. 2b and FIG. 4, electrodes 4 overlap each other by a predetermined distance. Needle access opening 16 is located generally above this overlap. Opening 16 extends through the top wall of housing 3 and first ceramic support substrate 1 and is generally circular in shape, and has a diameter slightly larger than the diameter of the typical hypodermic syringe 15. Opening 16 is positioned above the overlap of the electrodes 4 such that when the hypodermic syringe 15 is inserted into the opening 16, as discussed in more detail below, the shaft of the needle 17 of the hypodermic syringe 15 abuts the circumferential surface of proximal electrode 4a and the tip of the needle 17 contacts the upper surface of distal electrode 4b.

Located immediately below the electrodes 4, deflector insulator 2, and second ceramic support substrate 18, is needle debris box 12. Debris box 12 is a drawer-shaped rectangularly cubic component having a bottom wall and four upstanding side walls. Debris box 12 can be accessed from the front wall of housing 3 by sliding the box inward and outward of housing 3. As shown in greatest detail in FIG. 3 and FIG. 4, debris box 12 has a front to back dimension somewhat greater than the front to back dimension of deflector insulator 2 such that any matter falling on the downwardly sloping upper surface of deflector insulator 2 will slide off and will accumulate in debris box 12. As more fully discussed below, needle ash and other debris created during the destruction of the needle 17 falls onto the downwardly sloping upper surface of deflector insulator 2 and falls by gravity into debris box 12.

Located in the rearward portion of housing 3 is battery 9. Battery 9 can be any direct current electrical power source including, but not limited to, disposal batteries, rechargeable batteries, or an alternating current to direct current transformer. The negative terminal of battery 9 is electrically connected to copper pad 11a via lead wire 6a. Likewise, the positive terminal of battery 9 is electrically connected to copper pad 11b via lead wire 6b. As electrodes 4 are in electrical contact with shafts 7 and shafts 7 are in electrical contact with copper pads 11, and electrodes 4, shafts 7, and copper pads 11 are electrical conductors, direct electric current paths are created between the negative terminal of battery 9 and proximal electrode 4a through lead wire 6a, copper pad 11a, and shaft 7a, and from the negative terminal of battery 9 to distal electrode 4b through lead wire 6b, copper pad 11b, and shaft 7b, respectively. As discussed in more detail below, when hypodermic needle syringe 15 is inserted through opening 16 and needle 17 contacts both proximal electrode 4a and distal electrode 4b, a complete electric circuit is created defined by battery 9, lead wire 6a, copper pad 11a, shaft 7a, proximal electrode 4a, needle 17, distal electrode 4b, shaft 7b, copper pad 11b, lead wire 6b, back to battery 9. An access door may be located on housing 3 to allow access to battery 9. Likewise, the unit 20 can include an inboard battery charging means (not shown) or be connected to an external battery charging means, as known in the art. Likewise, if the power supply is a transformer from alternating current to direct current, the unit 20 will be supplied with a power cord (not shown).

Stop 5a is mounted to deflector insulator 2 and prevents proximal electrode 4a from moving downwardly more than a set distance along shaft 7a. Similarly, stop 5b is mounted on first ceramic support substrate 1 and prevents distal electrode 4b from moving more than a set distance upwardly along shaft 7b. Stops 5 also may include switches such that when proximal electrode 4a contacts stop 5a, power through the circuit is interrupted. Such switches are known in the art. Stops 5 also nudge the electrodes 4 when contacted, thus assisting in rotating electrodes 4 during each use. By rotating the electrodes 4, the electrodes will last longer.

Figure 3:
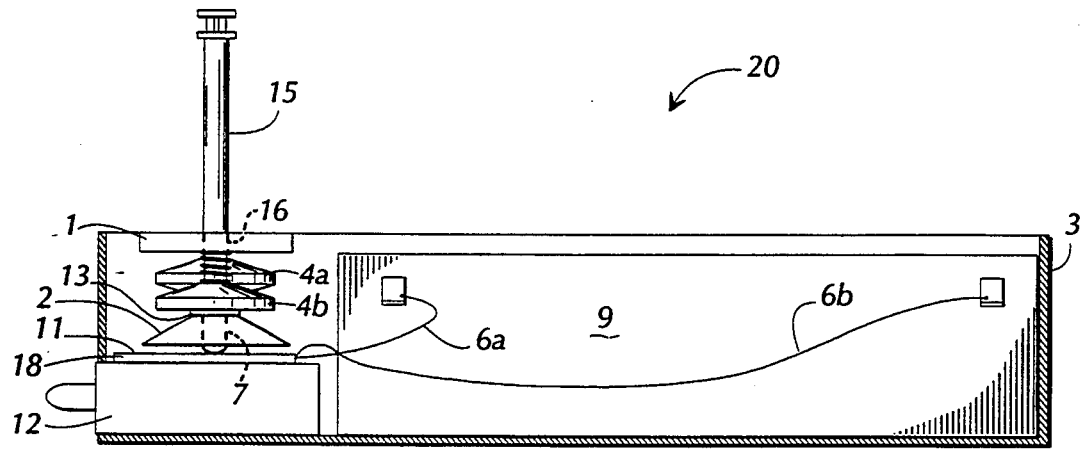
FIG. 3 is a perspective side view, partly in section, of the needle destroyer unit as in FIG. 1 in its starting and operating position showing a hypodermic needle with the metal needle portion inserted into the burner unit.

FIG. 3 also contains a representation of the electrical wiring diagram for the needle destroyer unit 20. The needle destroyer unit 20 preferably is operated by a battery 9, typically a 12-volt battery or two 6-volt batteries. The battery 9 may be recharged using a recharging means (not shown) which is plugged into a conventional 110-volt alternating current wall socket. The preferred current source is a rechargeable battery 9, or rechargeable batteries, capable of delivering up to 12-volts served by a low voltage DC battery charging source. Preferably, the needle destroyer unit 20 may include its own battery recharging means powered through an AC power cord. Various other power sources can be used and are known to one skilled in the power source art. Typically, currents ranging from 9 to 25 amperes at 3 to 6 volts, or up to 50 amperes at 12 volts, are adequate in most cases to incinerate hollow hypodermic metal needles of conventional size. The entire needle destroyer unit 20 is compact in size and self-contained and easily can be placed in an inconspicuous area within any medical office.

2. Sequence of Operation

Figure 2A:
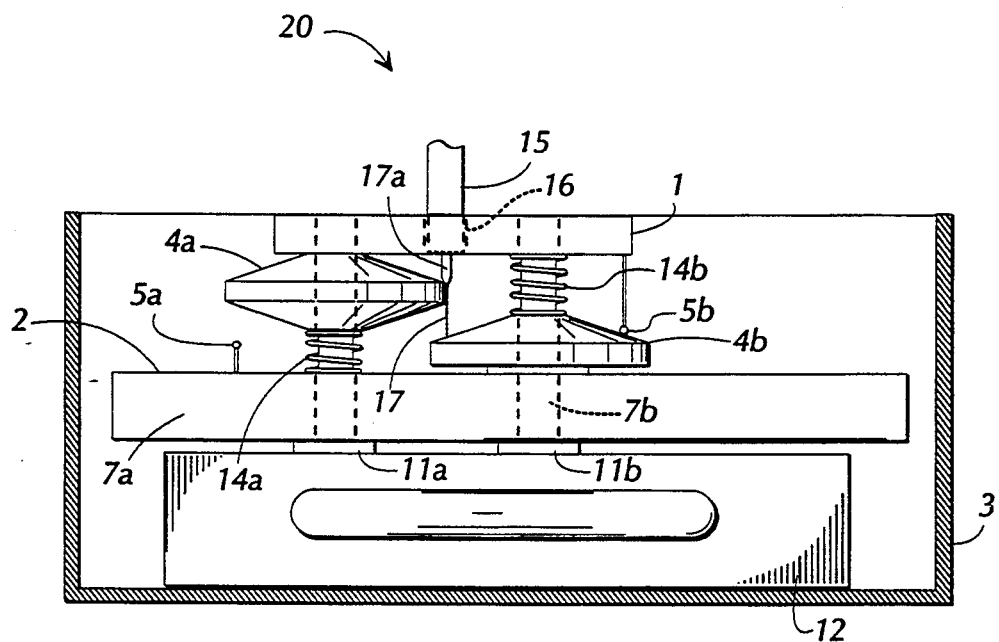
FIG. 2a is a perspective end view, partly in section, of the needle destroyer unit as in FIG. 1 in its starting and operating position showing a hypodermic needle with the metal needle portion inserted into the burner unit.
Figure 2B:
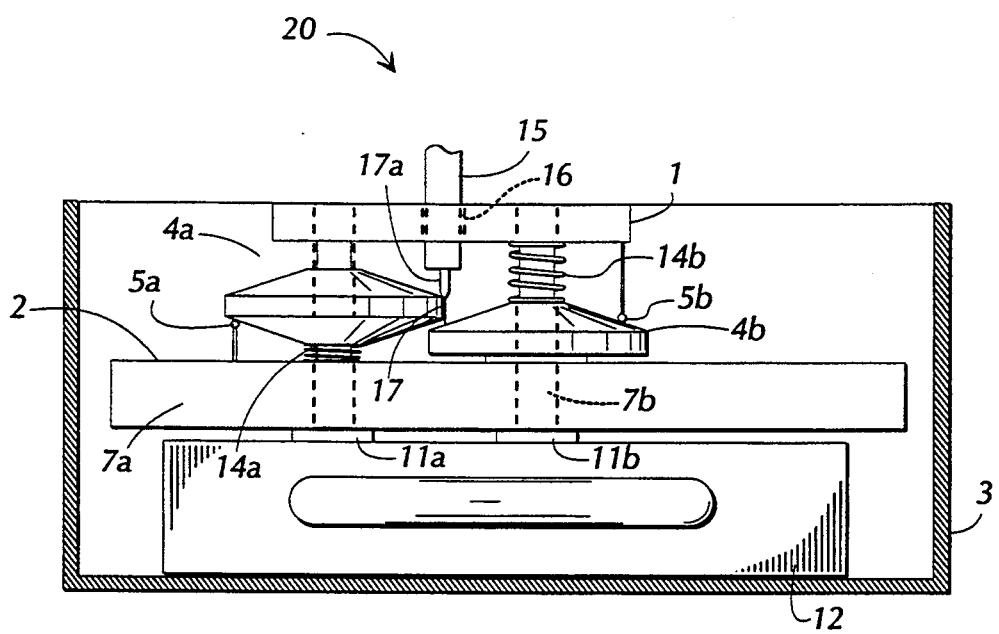
FIG. 2b is a perspective end view, partly in section, of the needle destroyer unit as FIG. 1 in its finishing position showing a hypodermic needle with the metal needle portion inserted into the burner unit.

With reference now in particular to FIGS. 2a and 2b, the sequence of operation of the syringe destroyer is described.

A used hypodermic needle syringe 15 is inserted, needle 17 first, into opening 16. The shaft of needle 17 contacts proximal electrode 4 and, as the needle 17 is inserted further into the unit 20, the tip of needle 17 contacts distal electrode 4b, completing the electrical circuit. As electricity runs through the circuit, needle 17 is heated by electrical resistance heating sufficient to incinerate the needle 17 and to sterilize any needle ash or melted needle portions falling from the incinerating needle 17.

As the tip of needle 17 is continuously incinerated, the syringe 15 is continuously inserted further into the unit 20, thus allowing continuous incineration of the needle 17. Where the needle 17 is attached to the syringe 15 typically is a nub portion 17a. Because proximal electrode 4a and distal electrode 4b are separated by a set distance of up to one-half inch ($\frac{1}{2}$"), and preferably approximately one-eighth to three-sixteenths of an inch ($\frac{1}{8}$"-3/16"), this length of needle 17 will remain when nub 17a contacts proximal electrode 4a. Because proximal electrode 4a is slidably mounted on shaft 7a and held in its upward position by compression spring 14a, when nub 17a contacts proximal electrode 4a, further downward pressure on the syringe 15 by the operator will cause proximal electrode 4a to slide downwardly on shaft 7a, compressing compression spring 14a. In this manner, proximal electrode 4a is forced downward and, therefore, closer to distal electrode 4b, thus shortening the gap between proximal electrode 4a and distal electrode 4b and allowing the incineration of the majority of the portion remaining of needle 17. Stop 5a prevents proximal electrode 4a from significant contact with distal electrode 4b so that neither electrode 4 is damaged by any such contact.

The ash created from the incineration of needle 17 falls downwardly by gravity onto deflector insulator 2. The lower surface of proximal electrode 4a and the upper surface of distal electrode 4b have downwardly tapering surfaces to allow any ash created by the incineration of the needle 17 to slide downwardly off of these surfaces onto deflector insulator 2. Likewise, any melted or other unincinerated portions of needle 17 will slide downwardly off of the electrode 4 surfaces onto deflector insulator 2. Such ash or other needle debris then will slide downwardly on the downwardly sloping upper surface of deflector insulator 2 into debris box 12. Debris box 12 can be removed from housing 3 at any time and the ash or other debris can be discarded.

The heat generated by the electrical circuit is sufficient to sterilize any ash or melted needle portion from needle 17. Therefore, the needle debris contained in debris box 12 is non-biohazardous and can be disposed of in any conventional manner. Likewise, the nub 17a and any other portion of needle 17 remaining on syringe 15 has been heated to a temperature high enough to sterilize. Therefore, the deneedled syringe 15 can be disposed of in any conventional manner.

Electrodes 4 may wear due to repeated usage. The electrodes 4 can be replaced by removing them from shafts 7 and substituting new electrodes 4. The relevant portions of the unit 20 are releasably secured to each other to allow such an exchange of electrodes 4, and other parts, if necessary. The electrodes 4 can spin freely on shafts 7 allowing electrodes 4 to turn with each use so that needle build-up or wear will not be in the same place on the electrodes 4 all of the time, which will greatly extend the electrode 4 life. Optionally, a small surfacer (not shown) may be included in the unit 20 to act upon the electrodes 4 to sweep off any build-up on the electrodes 4. Such a surfacer may be in the form of a brush, doctor blade, or any other surfacer which contacts the circumferential surfaces of the electrodes and the upper surface of distal electrode 4b. More than one surfacer may be used to allow greatest cleaning of the electrodes 4.

When the needle debris box 12 is full of needle refuse, for the most part ash, it can be removed from the housing 3. The needle refuse then can be disposed of in a correct manner. The refuse contained in the needle debris box 12 comprises non-biohazardous ash and, possibly, melted needle portions, all of which have been sterilized by the electrical resistance heat, and can be disposed of as ordinary trash. The syringe barrels then should be disposed of in a proper manner such as in a sharps' container or other biohazardous material disposal means.

The advantages of having such a needle destroyer apparatus 20 are numerous. The vaporization of the majority of the metal needle 17 and the sterilization of the remaining needle nub reduces the chance of needle sticks (puncture wounds). Even if such a needle stick occurs after the syringe 15 has been removed from the unit 20, the nub is sterile and therefore would not pass infection to whomever is handling the syringe. All points of access from the ambient to the interior of the syringe destroyer unit 20 may be lined with thermal resistant material, minimizing the escape of heat from the unit to the ambient. Likewise, the units may be shielded against radio frequency interruption so that the unit will not be a problem around sensitive equipment in the medical setting. The use of heat as the sterilization source, rather than chemicals, creates a more environmentally friendly unit and eliminates the risk of handling hazardous chemicals. The interior surfaces of the walls of housing 3 also may be lined with electrically insulative material, to prevent short-circuiting and inadvertent shocking of the operator.

In this manner, an apparatus for the destruction of syringe needles is provided. The present apparatus vaporizes the metal needle portion of a hypodermic needle syringe, thus rendering the hypodermic needle syringe safe to handle and to dispose. The above-detailed description of the preferred embodiments is for illustrative purposes only and is not meant to limit the spirit and scope of the invention and its equivalents as defined in the appended claims.

What is claimed is:

1. An apparatus for destroying or rendering safe metal needles having a shaft, hub and a tip comprising:
   first and second electrodes being generally disc shaped, each having an upper surface, a lower surface and a circumferential surface and spaced apart in an overlapping relationship to each other by a distance of up to about one-half of the length of the needle to be destroyed;
   a power source connected across to said first and second electrodes;
   a housing for said electrodes and said power source and having an opening for receiving the needle;
   wherein the needle is inserted into said opening of the housing so that the needle shaft contacts the circumferential surface of said final electrode at a point along the needle shaft up to approximately one-half inch (½") from the needle tip which contacts the upper surface of said second electrode to establish a flow of current through the portion of the needle shaft between said electrodes whereby said first electrode is initially located a distance of between approximately one-eighth of an inch and three-sixteenths of an inch (⅛"-3/16") from said second electrode until substantially all of the needle shaft is destroyed by electrical resistance of the shaft, with the first electrode being slidably movable toward the second electrode so that the needle shaft is displaced axially until substantially all of the remaining portion of the needle shaft is destroyed.

2. The apparatus as claimed in claim 1, further comprising a means for preventing said first electrode from moving toward said second electrode more than a predetermined distance.

3. The apparatus as claimed in claim 2, further comprising means for removing destroyed needle debris from said electrodes.

4. The apparatus as claimed in claim 3, wherein said electrodes are removable and replaceable.

5. The apparatus as claimed in claim 4, further comprising a means for slidably moving said first electrode away from said second electrode.

6. The apparatus as claimed in claim 5, wherein said first and second electrodes initially are spaced apart by a distance of from about one-eighth of an inch (⅛") to about three-sixteenths of an inch (3/16").

* * * * *